US012653455B1

(12) United States Patent
Rothschild

(10) Patent No.: US 12,653,455 B1
(45) Date of Patent: Jun. 16, 2026

(54) METHOD, WEARABLE DEVICE AND ELECTRONIC DEVICE FOR DETECTING UNINTENDED ONSET OF SLEEP (USL)

(71) Applicant: Leigh M. Rothschild, Miami, FL (US)

(72) Inventor: Leigh M. Rothschild, Miami, FL (US)

(73) Assignee: Horizon IP Technologies, LLC, Miami, FL (US)

( * ) Notice: Subject to any disclaimer, the term of this patent is extended or adjusted under 35 U.S.C. 154(b) by 0 days.

(21) Appl. No.: 19/205,676

(22) Filed: Jun. 24, 2025

(51) Int. Cl.
*A61B 5/00* (2006.01)
*A61M 21/00* (2006.01)
*G16H 40/67* (2018.01)

(52) U.S. Cl.
CPC .......... *A61B 5/4809* (2013.01); *A61B 5/6802* (2013.01); *A61B 5/746* (2013.01); *A61M 21/00* (2013.01); *G16H 40/67* (2018.01); *A61B 2562/02* (2013.01)

(58) Field of Classification Search
CPC ..... A61B 5/4809; A61B 5/6802; A61B 5/746; A61B 2562/02; G16H 40/67; A61M 21/00
USPC ........................................................ 340/575
See application file for complete search history.

(56) References Cited

U.S. PATENT DOCUMENTS

| | | | | |
|---|---|---|---|---|
| 9,955,925 B2 * | 5/2018 | Kannan | .................. | A61B 5/746 |
| 2010/0100004 A1 * | 4/2010 | van Someren | ....... | A61B 5/4818 |
| | | | | 600/595 |

| | | | | |
|---|---|---|---|---|
| 2011/0313259 A1 * | 12/2011 | Hatakeyama | ......... | B60W 40/08 |
| | | | | 600/300 |
| 2014/0143064 A1 | 5/2014 | Tran | | |
| 2014/0210625 A1 * | 7/2014 | Nemat-Nasser | ....... | G08B 21/06 |
| | | | | 340/575 |
| 2016/0035205 A1 * | 2/2016 | Messenger | ............. | G16H 40/67 |
| | | | | 340/539.15 |
| 2016/0287166 A1 | 10/2016 | Tran | | |
| 2017/0238868 A1 * | 8/2017 | Kenyon | ................. | G16H 50/20 |
| 2017/0265798 A1 * | 9/2017 | Sales | ...................... | G06V 20/35 |
| 2017/0311904 A1 | 11/2017 | Davis et al. | | |
| 2018/0033280 A1 | 2/2018 | Taylor | | |
| 2018/0053393 A1 | 2/2018 | White et al. | | |
| 2018/0229674 A1 | 8/2018 | Heinrich et al. | | |
| 2018/0348759 A1 | 12/2018 | Freeman et al. | | |
| 2019/0150820 A1 * | 5/2019 | Lee | ...................... | A61B 5/1118 |

(Continued)

*Primary Examiner* — Kerri L Mcnally
(74) *Attorney, Agent, or Firm* — Dobbin IP Law, P.C.; Geoffrey E. Dobbin

(57) ABSTRACT

The disclosure provides a system for detecting unintended sleep onset and issuing personalized warnings across multiple environments using wearable devices. This method integrates biometric sensors to continuously monitor physiological indicators of drowsiness, such as heart rate variability, eye movement, and micro-vibrations. Additionally, external sensors assess the user's real-time environmental context, including settings like moving vehicles or stationary workspaces. A machine learning-based sleep onset prediction model analyzes both physiological and environmental data to forecast the likelihood of unintended sleep. The model dynamically adjusts its sensitivity according to the user's context and delivers personalized alerts, such as vibrations, auditory cues, or visual notifications. These alerts are tailored to individual sleep patterns and environmental factors. The system continuously improves its predictions through feedback from the user, while displaying relevant information on a user interface for enhanced guidance.

10 Claims, 4 Drawing Sheets

(56) References Cited

U.S. PATENT DOCUMENTS

| | | | |
|---|---|---|---|
| 2020/0315480 A1 | 10/2020 | Hwang | |
| 2021/0169417 A1* | 6/2021 | Burton | A61B 5/4857 |
| 2022/0079512 A1* | 3/2022 | Despenic | A61B 5/7275 |
| 2022/0327905 A1* | 10/2022 | Rothschild | A61B 5/0022 |
| 2025/0222934 A1* | 7/2025 | Ren | G06V 40/10 |

* cited by examiner

100

Electronic device 106

Wearable device 108

METHOD, WEARABLE DEVICE AND ELECTRONIC DEVICE FOR DETECTING UNINTENDED ONSET OF SLEEP (USL)

TECHNICAL FIELD

The present disclosure pertains to methods, wearable devices and systems that are designed for real-time detection and prevention of unintended sleep onset (USL). Specifically, present disclosure integrates biometric sensors and environmental context analysis to continuously monitor physiological indicators of drowsiness, such as heart rate variability, eye movement, and micro-vibrations.

BACKGROUND

In various industries and daily activities, unintended sleep onset (USL) poses a significant risk to safety, performance, and well-being, particularly in environments where sustained alertness is critical, such as driving, operating machinery, or performing complex tasks. Traditional drowsiness detection systems often rely on limited indicators, such as eye movement or simple inactivity, without considering a comprehensive range of physiological and environmental data. These systems tend to produce high rates of false positives or miss early signs of sleep onset, especially when users are in dynamic environments like moving vehicles, classrooms, or workspaces. Furthermore, conventional systems do not account for individual variations in sleep patterns, leading to generic, one-size-fits-all alerts that may not be effective for all users.

Another key challenge is the lack of adaptability in existing systems. Many devices fail to differentiate between high-risk and low-risk environments, such as driving versus working at a desk, which can lead to inappropriate alert thresholds. This lack of contextual awareness diminishes the effectiveness of these systems, resulting in either an over-abundance of alerts in low-risk environments or insufficient warnings in high-risk situations. Moreover, current systems often do not provide a feedback loop, meaning they cannot improve their accuracy over time based on user data and behavior.

Conventional methods for addressing the problem of unintended sleep onset (USL) detection typically rely on limited technologies, such as single biometric indicators or basic environmental triggers. For instance, many traditional systems use eye-tracking cameras or wearable devices that monitor heart rate or physical inactivity to detect drowsiness. While these methods provide some insight into a user's state of alertness, they often lack the ability to combine multiple data points, such as heart rate variability, eye movement, and micro-vibrations, leading to lower accuracy in detecting the early stages of sleep onset. Furthermore, many conventional systems fail to account for environmental context, such as whether a user is in a moving vehicle, sitting in a stationary workspace, or in a classroom. As a result, these systems may produce numerous false positives in low-risk environments where brief periods of inactivity do not indicate drowsiness. Conversely, in high-risk situations, like driving, these systems may miss critical cues due to their inability to adjust sensitivity based on the environment.

Another significant shortcoming is the lack of personalization in conventional systems. These methods often apply generic thresholds and alert mechanisms without considering the user's individual sleep patterns, preferences, or past behavior. This can lead to ineffective alerts that are either too frequent and annoying or too weak to prevent accidents. Moreover, traditional systems do not incorporate adaptive learning mechanisms, meaning they do not improve over time based on user feedback or historical data, which limits their long-term effectiveness. Ultimately, the inability of conventional methods to combine physiological and environmental data, adapt to different contexts, and provide personalized, evolving warnings makes them inadequate for ensuring user safety across multiple environments.

As a result, there is a need for a method, a wearable device and an electronic device for detecting unintended onset of sleep (USL) and providing warnings to a user across multiple environments in a substantially improved manner.

Further limitations and disadvantages of conventional and traditional approaches will become apparent to one of skill in the art, through comparison of described systems with some aspects of the present disclosure, as set forth in the remainder of the present application and with reference to the drawings.

SUMMARY

According to embodiments disclosed herein, the electronic device includes a processor, and memory, communicatively coupled to the processor is disclosed. In an embodiment, the processor of a wearable device integrates a plurality of biometric sensors into the wearable device. In an embodiment, the plurality of biometric sensors is configured to continuously monitor one or more physiological indicators of drowsiness associated with a user. In an embodiment, one or more physiological indicators comprise heart rate variability, eye movement, and micro-vibrations. In an embodiment, the processor assesses the real-time environmental context of a user's environment by integrating data from one or more external sensors to distinguish between different environmental contexts. In an embodiment, the real-time environmental context comprises a moving vehicle, a stationary workspace, and a classroom. In an embodiment, one or more external sensors comprise GPS, accelerometers, and ambient light sensors. In an embodiment, the processor adapts a sleep onset prediction model based on one or more machine learning techniques to predict a likelihood of unintended sleep onset by analyzing one or more physiological indicators and the environmental context. In an embodiment the sleep onset prediction model is configured to dynamically adjust a sensitivity based on the real-time environmental context and the processor provides, a personalized alert based on sleep patterns and preferences associated with the user. In an embodiment, the personalized alert comprises a vibration, an auditory cue, and a visual notification which is tailored to the user's environment and historical sleep behaviour. The processor continuously updates the sleep onset prediction model based on feedback from the user and outcomes of prior personalized alerts to improve the accuracy of future predictions and the processor displays information associated with the personalized alert on a user interface for guiding the user with visual cues.

BRIEF DESCRIPTION OF DRAWINGS

The accompanying drawings illustrate the various embodiments of systems, methods, and other aspects of the disclosure. Any person of ordinary skill in the art will understand that the depicted element boundaries (e.g., boxes, groups of boxes, or other shapes) in the figures are an example of the boundaries. In some examples, one element may be configured as multiple elements, or multiple elements may be configured as one element. In some examples, an element shown as an internal component of one element may be implemented as an external component in another element, and vice versa. Furthermore, the elements may not be drawn to scale. Various embodiments will hereinafter be described in accordance with the appended drawings, which are provided to illustrate and not to limit the scope in any manner, wherein similar designations denote similar elements, and in which.

DETAILED DESCRIPTION

Figure 1:
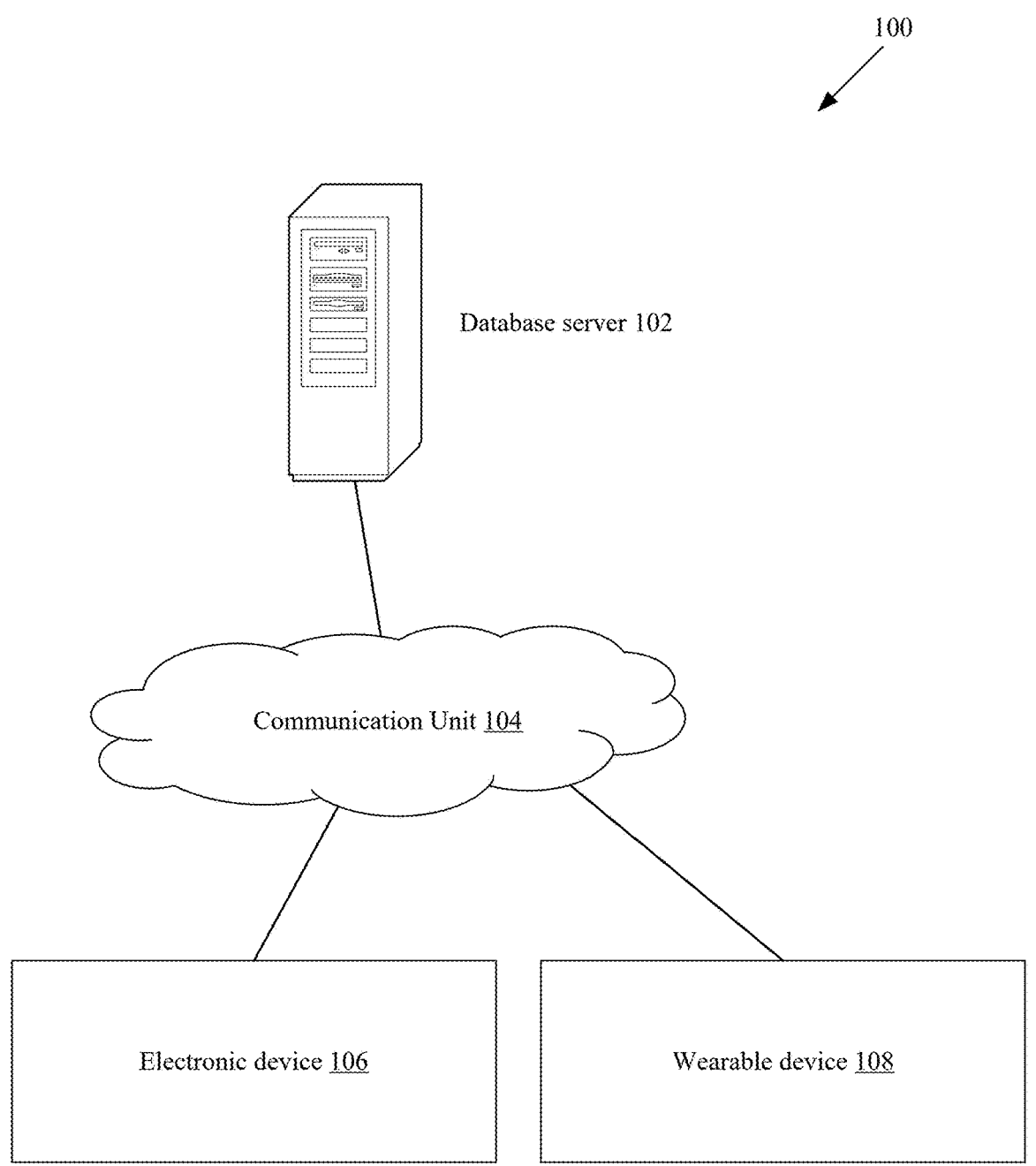
FIG. 1 is a block diagram that illustrates a system environment in which various embodiments of the method and the system may be implemented.

The present disclosure may be best understood with reference to the detailed figures and description set forth herein. Various embodiments are discussed below with reference to the figures. However, those skilled in the art will readily appreciate that the detailed descriptions given herein with respect to the figures are simply for explanatory purposes as the methods and systems may extend beyond the described embodiments. For example, the teachings presented, and the needs of a particular application may yield multiple alternative and suitable approaches to implement the functionality of any detail described herein. Therefore, any approach may extend beyond the implementation choices in the following embodiments described and shown.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

The primary objective of the present disclosure is to provide a reliable and accurate system for detecting unintended sleep onset (USL) and delivering timely warnings to users in various environments, such as driving, working, or attending educational settings. The present disclosure aims to continuously track both physiological indicators of drowsiness and external factors, allowing for more precise predictions of sleep onset, by integrating a range of biometric sensors and environmental monitoring tools. Another objective is to enhance user safety and performance by dynamically adjusting alert thresholds based on the detected environment, reducing false positives in low-risk situations while ensuring heightened sensitivity in high-risk environments like driving.

Additionally, the present disclosure seeks to offer a personalized user experience by customizing the warning mechanisms based on individual sleep patterns, preferences, and historical behavior, ensuring that alerts are both effective and minimally intrusive. The system is designed to learn and adapt over time through continuous feedback, refining its predictive capabilities and reducing the likelihood of missed drowsiness detection. Furthermore, the present disclosure aims to provide a versatile solution that can be used across multiple wearable devices, such as smartwatches, glasses, or rings, and can notify third parties when necessary to further mitigate risks associated with unintended sleep.

The system predicts the likelihood of sleep onset and provides personalized warnings to the user through customized alerts, including vibrations, auditory cues, and visual notifications, using machine learning techniques. The present disclosure is applicable across various environments, such as vehicles, workspaces, and classrooms, and is designed to dynamically adapt its sensitivity based on environmental conditions to enhance user safety and alertness. The technical problem addressed by this disclosure is the challenge of accurately detecting unintended sleep onset (USL) in different settings and providing timely, personalized alerts to prevent accidents or loss of focus. Conventional systems often lack the capability to continuously monitor both physiological and environmental factors in real-time, leading to inaccurate drowsiness detection and ineffective warnings. This system overcomes these limitations by integrating multiple biometric and external sensors to evaluate the user's physiological state and environmental context. Machine learning enables the system to adjust its sensitivity dynamically based on the environment, reducing false positives and improving the accuracy of sleep onset predictions. Furthermore, it delivers personalized warnings tailored to individual sleep patterns and preferences, ensuring timely alerts in high-risk scenarios like vehicle operation or environments where maintaining alertness is crucial.

The present disclosure addresses these challenges by integrating advanced biometric and environmental sensors into wearable devices, combined with machine learning techniques that adapt to both physiological states and environmental contexts. The system provides more accurate predictions of unintended sleep onset and delivers personalized, environment-specific warnings. The present disclosure's continuous learning capability, along with user-specific customization, ensures more timely and relevant alerts, significantly reducing the risk of accidents, enhancing performance, and improving user safety across different environments by analyzing real-time data from multiple sources.

The present disclosure is a wearable system designed to detect unintended sleep onset (USL) and provide timely warnings to users across diverse environments. The present disclosure integrates a range of biometric sensors such as heart rate variability, eye movement, and micro-vibrations to continuously monitor physiological indicators of drowsiness. Additionally, external sensors, including GPS, accelerometers, and ambient light sensors, are used to assess the environmental context in real-time, distinguishing between situations like driving, working in a stationary space, or attending a class. The system employs a machine learning-based sleep onset prediction technique that dynamically adjusts its sensitivity based on the user's current environment, ensuring more accurate detection of drowsiness.

The system offers personalized warnings, delivering alerts via vibration, auditory cues, or visual notifications, all tailored to the user's specific sleep patterns and preferences, to further enhance usability. The present disclosure adapts these alerts according to the risk level of the environment, increasing sensitivity in high-risk situations, such as while driving, and lowering it in low-risk settings like desk work. The present disclosure also incorporates a feedback loop, continuously updating the sleep prediction technique based on user responses and previous alert outcomes, improving accuracy over time. Additionally, the system can notify third parties, such as supervisors or instructors, in non-driving environments where unintended sleep may affect performance.

FIG. 1 is a block diagram that illustrates a system environment in which various embodiments of the method and the system may be implemented. System environment 100 typically includes a database server 102, a communication unit 104, an electronic device 106 and wearable device 108 which are typically communicatively connected via the communication network 104.

The database server 102 in the present disclosure serves as a central hub for managing and storing the vast amounts of data generated by the wearable device's sensors. The database server 102 is responsible for collecting and organizing both physiological data, such as heart rate variability, eye movement, and micro-vibrations, as well as environmental data from sources like GPS, accelerometers, and ambient light sensors. This data is then processed and stored in the database server, where it can be accessed for real-time analysis or used to refine the sleep onset prediction model over time. The database server 102 also stores user-specific data, including historical sleep patterns, alert preferences, and feedback from previous instances of unintended sleep detection.

Through secure connections, the database server 102 communicates with wearable devices to update the machine learning technique and deliver personalized alerts. Additionally, database server 102 can store and manage data for third-party notifications, ensuring a seamless integration between the system's detection capabilities and external parties.

The communication unit 104 facilitates data exchange between the wearable device and external systems, ensuring the seamless operation of the present disclosure. The present disclosure is responsible for transmitting real-time physiological and environmental data from the wearable device to the database server 102, where it is processed and analysed. The communication unit 104 uses wireless communication protocols, such as Bluetooth, Wi-Fi, or cellular networks, to ensure continuous connectivity, enabling real-time updates to the machine learning technique and the delivery of alerts. The communication unit 104 also allows the wearable device to receive updates, such as refinements to the sleep onset prediction model or adjustments to the user's alert preferences, ensuring the system remains adaptive and personalized. In addition to connecting with the database server 102, the communication unit 104 enables interactions with third-party systems, allowing notifications to be sent to supervisors, family members, or other designated individuals when unintended sleep is detected in high-risk or monitored environments.

Electronic device 106 in the present disclosure refers to the wearable system, such as a smartwatch, smart glasses, or smart ring, that houses the essential hardware components required for detecting unintended sleep onset (USL) and delivering personalized warnings. The present disclosure integrates multiple biometric sensors to continuously monitor physiological indicators like heart rate variability, eye movement, and micro-vibrations, while also incorporating external sensors such as GPS, accelerometers, and ambient light sensors to assess the user's environmental context. The electronic device 106 is powered by a processor that manages data collection and analysis in real time, enabling the system to predict the likelihood of sleep onset based on a machine learning technique. Additionally, electronic device 106 features a user interface that displays visual notifications and provides feedback to the user about their drowsiness levels. Through this interface, the device also delivers personalized warnings via vibration, sound, or visual cues, ensuring the user remains alert in various environments.

The wearable device 108 is the primary component of the present disclosure designed to detect unintended sleep onset (USL) and provide personalized warnings to the user. This device can take various forms, such as a smartwatch, smart glasses, or a smart ring, and is equipped with multiple biometric sensors that monitor physiological signals like heart rate variability, eye movement, and micro-vibrations. These sensors work in tandem with external sensors, such as GPS, accelerometers, and ambient light detectors, to continuously assess the user's physical state and surrounding environment in real time. The wearable device 108 houses a processor that runs a machine learning-based technique to predict sleep onset, dynamically adjusting its sensitivity based on the user's context-whether they are driving, working, or resting. Additionally, the wearable device 108 features a personalized warning system that delivers customized alerts through vibrations, auditory signals, or visual notifications, based on the user's preferences and their unique sleep patterns. The wearable device's 108 lightweight and portable design make the wearable device an ideal tool for users in various environments, offering a seamless experience while enhancing safety and productivity.

Figure 2:
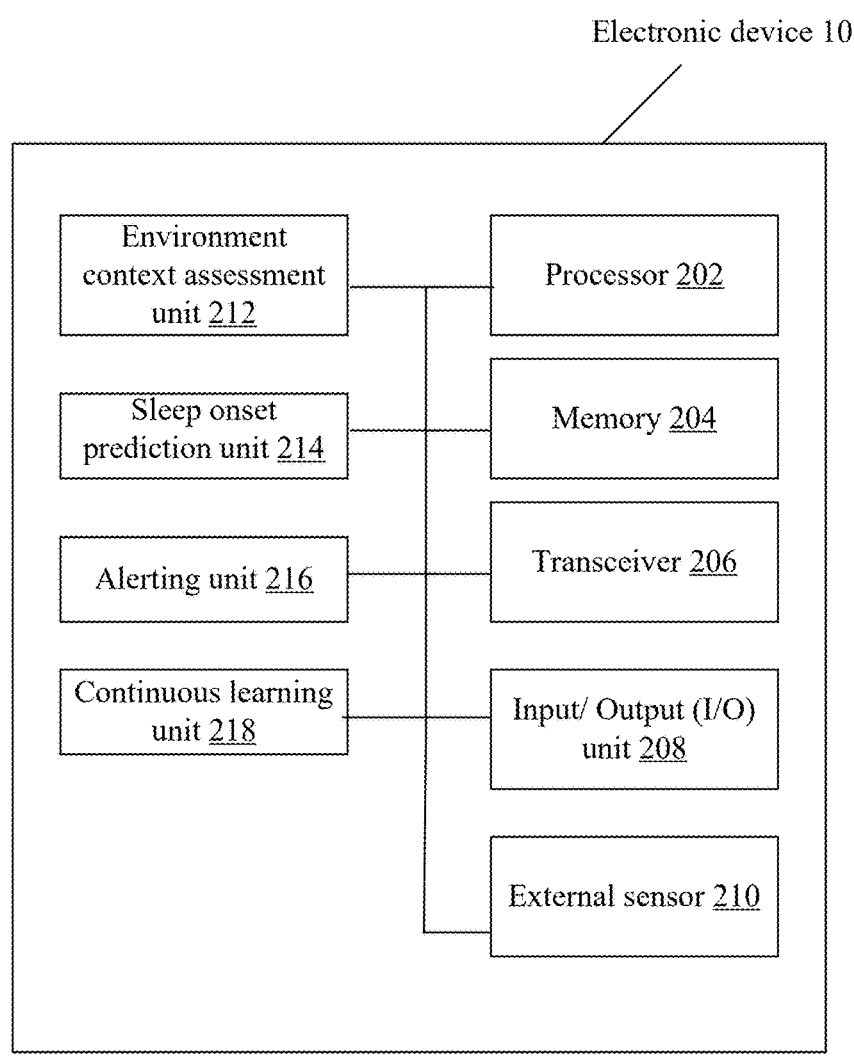
FIG. 2 is a block diagram that illustrates an electronic device configured to detect unintended onset of sleep (USL) and provides warnings to a user across multiple environments, in accordance with an embodiment of present disclosure.

FIG. 2 is a block diagram that illustrates an electronic device configured to detect unintended onset of sleep (USL) and provides warnings to a user across multiple environments, in accordance with an embodiment of present disclosure. FIG. 2 is explained in conjunction with elements of FIG. 1. Here, the electronic device 106 preferably includes a processor 202, a memory 204, a transceiver 206, an input/output unit 208, body external sensor 210, environmental context assessment unit 212, sleep onset prediction unit 214, altering unit 216, continuous learning unit 218.

Both the electronic device (FIG. 2) and the wearable device (FIG. 3) comprise similar components, including a processor, transceiver, memory, and input/output devices. To avoid redundancy, these components are described collectively.

Processor 202 comprises suitable logic, circuitry, interfaces, and/or code that may be configured to execute a set of instructions stored in memory 204 and may be implemented based on various technologies known in the art for the processor 202. The processor 202 operates works in coordination with the transceiver 206, the input/output unit 208, body external sensor 210, environmental context assessment unit 212, sleep onset prediction unit 214, altering unit 216, continuous learning unit 218, Biometric sensor 310, Cognitive Stimulus unit 312. Examples of the processor 202 include, but are not limited to, an X86-based processor, a Reduced Instruction Set Computing (RISC) processor, an Application-Specific Integrated Circuit (ASIC) processor, and a Complex Instruction Set Computing (CISC) processor.

Memory 204 includes suitable logic, circuitry, interfaces, and/or code that may be configured to store the set of instructions, executed by processor 202. Preferably, memory 204 is configured to store one or more programs, routines, or scripts that are executed in coordination with processor 202. In addition, memory 204 may be implemented based on random access memory (RAM), a read only memory (ROM), a hard disk drive (HDD), a storage server, and/or a secure digital (SD) card.

Transceiver 206 comprises suitable logic, circuitry, interfaces, and/or code that may be configured to receive one or more attributes associated with external sensor 210 and biometric sensors 310. Transceiver 206 enables wireless communication capabilities that allow the device to connect to Wi-Fi networks, Bluetooth-enabled devices, or cellular networks. This connectivity facilitates data exchange, firmware updates, and remote configuration. Transceiver 206 serves as an interface for sending and receiving data packets via wireless networks. This includes exchanging information with other devices, accessing online resources, and transferring data to and from remote servers. The Transceiver 206 supports various network protocols and standards, ensuring compatibility with different communication technologies. This versatility enables seamless integration into existing network infrastructures. Transceiver 206 can provide adjustable transmission power and bandwidth settings, allowing the device to optimize communication range and data transmission speeds according to environmental conditions and network requirements. Transceiver 206 has security features such as encryption, authentication, and data integrity checks to ensure secure communication over wireless networks. This protects sensitive information and prevents unauthorized access. The transceiver 206 could be implemented as a hardware module in the electronic device 106, which includes radio frequency (RF) components, antennas, and signal processing circuitry. Alternatively, it could be integrated into the device's system-on-chip (SoC) or connect as a separate module via interfaces such as USB or PCIe.

Input/output unit 208 comprises suitable logic, circuitry, interfaces, and/or code that may be configured to receive one or more attributes associated with detecting unintended onset of sleep (USL) and providing warnings to a user across multiple environments. Input/output unit 208 includes components such as buttons, touchscreens, or touchpads that serve as user interfaces for interacting with the device. These interfaces allow the user to enter commands, trigger actions and navigate through menus. A screen, such as an LCD or OLED screen, is part of input/output unit 208 and provides visual feedback to the user. Input/output unit 208 displays decoded information, user notifications, augmented reality (AR) overlays, and other graphical elements. The input/output unit 208 could be implemented as a combination of hardware components, including button ns, touchscreens, speakers, microphones, and connectors, integrated into the physical design of the device. Additionally, software components would work with these hardware elements to manage the functions of the input/output unit 208 and user interaction. Input/output unit 208 comprises of various input and output devices configured to communicate with the processor 202. Examples of input devices include but are not limited to, a keyboard, a mouse, a joystick, a touch screen, a microphone, a camera, and/or a docking station. Examples of the output devices include, but are not limited to, a display screen and/or a speaker.

The external sensor 210 comprises suitable logic, circuitry, interfaces, and/or code that may be configured to receive one or more attributes associated with detecting unintended onset of sleep (USL) and providing warnings to a user across multiple environments. The external sensor 210 integrated into the electronic device plays a vital role in enhancing the system's ability to detect unintended sleep onset (USL) by monitoring environmental factors in real time. These sensors include GPS, accelerometers, ambient light detectors, and other location or motion-based technologies that gather data about the user's surroundings. The GPS sensor helps determine whether the user is in motion, such as driving or walking, while the accelerometer tracks movement patterns, identifying whether the user is in a stationary or active state. Ambient light sensors contribute by detecting changes in lighting conditions, which can help assess whether the user is in an indoor or outdoor environment, or if they are transitioning between day and night. These external sensors 210 complement the biometric data collected from the user's physiological indicators, providing a broader context for the machine learning technique to make accurate predictions about potential sleep onset. For instance, in high-risk environments like driving, the external sensor 210 can trigger a heightened sensitivity in the prediction model, ensuring that the user receives timely and personalized alerts based on both their physical and environmental states. This comprehensive data input allows the system to dynamically adjust its response, making the external sensor 210 a crucial component of the overall system's effectiveness in preventing unintended sleep onset.

The environmental context assessment unit 212 comprises suitable logic, circuitry, interfaces, and/or code that may be configured to receive one or more attributes associated with detecting unintended onset of sleep (USL) and providing warnings to a user across multiple environments. The environmental context assessment unit 212 is a critical component of the invention that analyses and interprets real-time data from external sensors to determine the user's surrounding environment. The environmental context assessment unit 212 integrates information from sources such as GPS, accelerometers, and ambient light sensors to build an accurate profile of the user's environment, whether they are in a moving vehicle, a stationary workspace, or an outdoor area. By assessing factors like location, motion, and light levels, the unit can distinguish between different contexts, such as identifying when the user is driving or working in a low-activity setting. This contextual understanding enables the system to adjust its sensitivity to unintended sleep onset based on the risk level associated with the environment. For example, if the environmental context assessment unit detects that the user is in a high-risk environment, such as driving or operating heavy machinery, it increases the system's alert thresholds to ensure more immediate warnings. Conversely, in low-risk environments, such as sitting at a desk, the system can lower the sensitivity to reduce false positives. The environmental context assessment unit 212 ensures that the sleep onset detection process remains highly accurate and relevant to the user's current situation, by dynamically adjusting the system's behavior based on environmental factors.

The sleep onset prediction unit 214 comprises suitable logic, circuitry, interfaces, and/or code that may be configured to receive one or more attributes associated with detecting unintended onset of sleep (USL) and providing warnings to a user across multiple environments. The sleep onset prediction unit 214 within the electronic device 106 is a sophisticated system designed to analyse real-time data and predict the likelihood of unintended sleep onset (USL). This component relies on a machine learning-based technique that processes data from various biometric sensors integrated into the device, such as heart rate variability, eye movement, and micro-vibrations. The system can identify patterns and deviations that suggest the user may be experiencing early signs of drowsiness, by continuously monitoring these physiological indicators.

The alerting unit 216 comprises suitable logic, circuitry, interfaces, and/or code that may be configured to receive one or more attributes associated with detecting unintended onset of sleep (USL) and providing warnings to a user across multiple environments. The alerting unit 216 in the electronic device 106 is a key feature responsible for delivering timely and effective warnings to the user when unintended sleep onset (USL) is detected. The alerting unit 216 is designed to provide personalized alerts through multiple channels, including vibrations, auditory signals, and visual notifications. When the sleep onset prediction technique identifies a heightened risk of drowsiness, the alerting unit 216 activates its various notification mechanisms based on user preferences and the context of the detected environment. For instance, if the system detects a high risk of drowsiness while driving, the alerting unit 216 may initiate a strong vibration pattern to immediately capture the user's attention, accompanied by a loud auditory signal to ensure the warning is noticeable over ambient noise. In contrast, during low-risk activities, such as sitting at a desk, the alerting unit 216 might opt for a more subtle vibration or visual alert on the device's screen to minimize disruption. The alerting unit 216 is also capable of adjusting the intensity and type of alerts based on user feedback, historical data, and real-time context, allowing for a customized approach that balances effectiveness with user comfort. Additionally, the alerting unit 216 can integrate with other system components to provide layered notifications, such as combining vibrations with visual cues or sending messages to a connected smartphone app. This multi-faceted approach ensures that the user receives appropriate and effective warnings tailored to their specific needs and environment, enhancing overall safety and responsiveness to drowsiness.

The continuous learning unit 218 comprises suitable logic, circuitry, interfaces, and/or code that may be configured to receive one or more attributes associated with detecting unintended onset of sleep (USL) and providing warnings to a user across multiple environments. The continuous learning unit 218 in the electronic device 106 is an advanced feature designed to enhance the accuracy and effectiveness of the sleep onset prediction system over time. This continuous learning unit 218 leverages machine learning technique to continuously analyze and integrate data from various sources, including physiological indicators and environmental context. As the device collects more data from the user's daily activities, the continuous learning unit 218 processes this information to refine and improve the prediction model. Continuous learning unit 218 continuously updates the technique based on feedback from the user and the outcomes of previous alerts, learning from instances when drowsiness was accurately or inaccurately predicted. This iterative process allows the system to adjust its sensitivity and alert thresholds dynamically, making the predictions more precise and relevant to the user's evolving sleep patterns and environmental conditions. For example, if the system identifies that certain patterns of physiological data frequently precede drowsiness in specific environments, it can adjust its predictive model to better anticipate and respond to these patterns in the future. The continuous learning unit 218 also incorporates contextual data, such as changes in the user's activity levels or environment, into its learning process. The continuous learning unit 218 ensures that the system remains adaptable and responsive to new information, enhancing its ability to provide timely and accurate warnings, by doing so.

Figure 3:
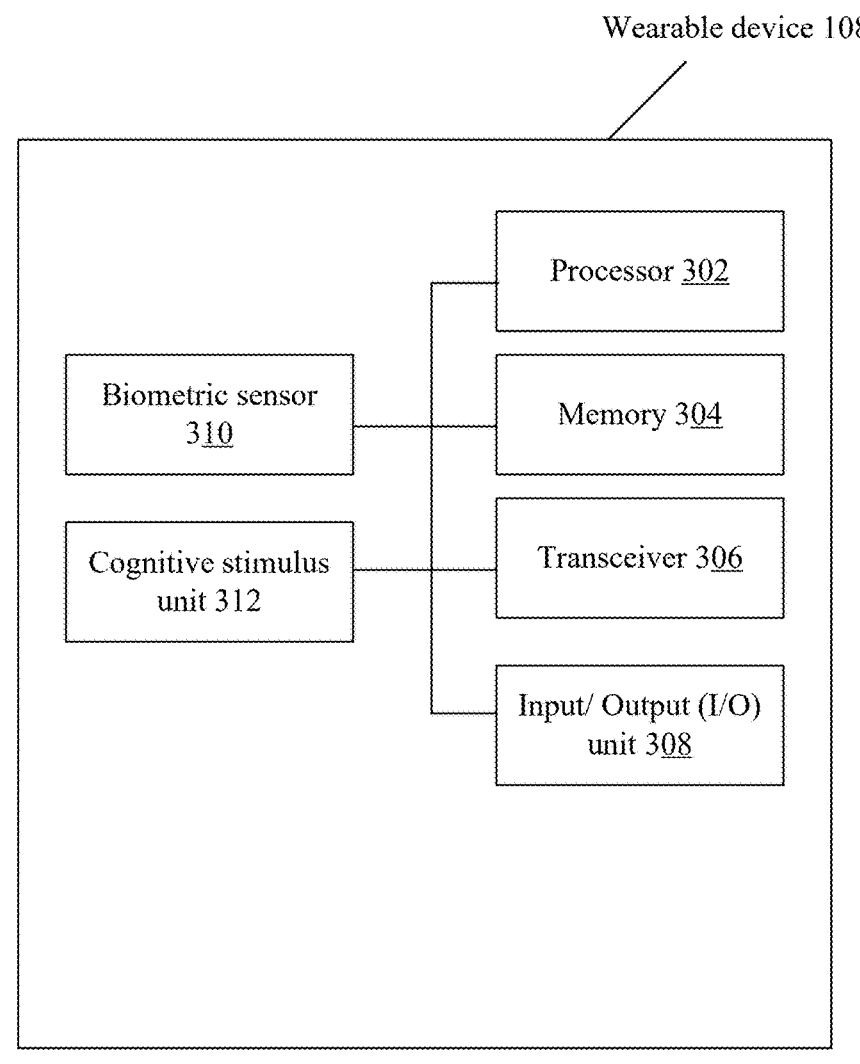
FIG. 3 is a block diagram that illustrates the wearable device configured to detect unintended onset of sleep (USL) and providing warnings to a user across multiple environments, in accordance with an embodiment of present disclosure.

FIG. 3 is a block diagram that illustrates the wearable device configured to detect unintended onset of sleep (USL)

and providing warnings to a user across multiple environments, in accordance with an embodiment of present disclosure.

The biometric sensor 310 in the wearable device 108 comprises suitable logic, circuitry, interfaces, and/or code that may be configured to receive one or more attributes associated with detecting unintended onset of sleep (USL) and providing warnings to a user across multiple environments. The biometric sensor 310 in the wearable device 108 is a fundamental component responsible for monitoring and analyzing various physiological indicators that signal potential unintended sleep onset (USL). This sensor is designed to track key metrics such as heart rate variability, eye movement, and micro-vibrations, providing crucial data for assessing the user's state of drowsiness. The heart rate variability sensor measures fluctuations in the time interval between heartbeats, which can indicate changes in autonomic nervous system activity associated with drowsiness. The eye movement sensor uses infrared technology or similar methods to monitor blink rate and eye closure patterns, which are critical indicators of fatigue and potential sleep onset. Additionally, the micro-vibration sensor detects subtle movements or vibrations in the user's wrist or other areas, which can also be indicative of decreased alertness.

The biometric sensor 310 continuously collects data in real-time, feeding this information into the device's predictive technique and alerting systems. The sensor helps build a comprehensive profile of the user's alertness level, by integrating these physiological signals. This data is then used to determine when to trigger personalized warnings, ensuring that alerts are based on accurate and timely assessments of the user's drowsiness. The precision and reliability of the biometric sensor 310 are essential for the system's effectiveness in preventing unintended sleep onset and enhancing overall safety and user experience.

The stimulus unit 312 in the wearable device 108 comprises suitable logic, circuitry, interfaces, and/or code that may be configured to receive one or more attributes associated with detecting unintended onset of sleep (USL) and providing warnings to a user across multiple environments. The stimulus unit 312 in the wearable device 108 is a critical feature designed to engage the user's attention and counteract drowsiness when potential unintended sleep onset (USL) is detected. This unit provides cognitive and sensory stimuli to re-engage the user's focus and help prevent sleep. It includes various mechanisms such as auditory cues, visual prompts, and interactive mental challenges tailored to the user's preferences and the context of the situation. When the system detects early signs of drowsiness, the stimulus unit 312 activates non-distracting mental challenges or auditory stimuli. These challenges may include simple cognitive tasks, such as quick mental arithmetic or memory games, which are designed to stimulate the user's brain without causing significant distraction. Auditory cues, such as gentle but noticeable sounds or tones, can also be used to capture the user's attention and prompt them to take corrective actions.

The stimulus unit 312 is designed to deliver these stimuli in a way that is integrated with the wearable device's other alert mechanisms, ensuring that the user receives a cohesive and effective response to drowsiness. For instance, if the system triggers a vibration alert due to detected drowsiness, the stimulus unit 312 might simultaneously present a visual cue or an interactive task on the device's screen. This multi-modal approach helps ensure that the user remains engaged and alert, reducing the likelihood of unintended sleep and enhancing overall safety and productivity.

In an exemplary operation, the processor of a wearable device integrates a plurality of biometric sensors into the wearable device. In an embodiment, the plurality of biometric sensors is configured to continuously monitor one or more physiological indicators of drowsiness associated with a user. In an embodiment, the one or more physiological indicators comprises a heart rate variability, an eye movement, and a micro-vibration. In an embodiment, the processor assesses the real-time environmental context of a user's environment by integrating data from one or more external sensors to distinguish between different environmental contexts. In an embodiment, the real-time environmental context comprises a moving vehicle, a stationary workspace, and a classroom.

In an embodiment, the one or more external sensors comprises GPS, accelerometers, and ambient light sensors. The processor adapts a sleep onset prediction model based on one or more machine learning techniques to predict a likelihood of unintended sleep onset by analyzing real-time the one or more physiological indicators and the environmental context. In an embodiment, the sleep onset prediction model is configured to dynamically adjust a sensitivity based on the real-time environmental context and the processor provides a personalized alert based on sleep patterns and preferences associated with the user. In an embodiment, the personalized alert comprises a vibration, an auditory cue, and a visual notification which is tailored to the user's environment and historical sleep behavior.

The processor continuously updates the sleep onset prediction model based on feedback from the user and outcomes of prior personalized alerts to improve the accuracy of future predictions and the processor displays information associated with the personalized alert on a user interface for guiding the user with visual cues. In an embodiment, the wearable devices are a smartwatch, smart glasses, smart ring. In an embodiment, the sleep onset prediction model increases alertness thresholds while detecting that the user is in a high-risk environment. In an embodiment, the environmental context analysis unit distinguishes between high-activity and low-activity environments by monitoring environmental triggers such as prolonged inactivity or changes in ambient light. In an embodiment, the personalized alert is configured to provide customizable alerts based on the user's preferences, including adjusting the intensity of vibration or auditory cues. In an embodiment, the wearable device is further configured to notify a third party comprising a supervisor or instructor, when the unintended sleep onset is detected in non-driving environments.

In an embodiment, further comprising a cognitive stimulus unit configured to provide non-distracting mental challenges or auditory cues designed to re-engage the user's focus when detected as stationary and drowsy. In an embodiment, the sleep onset prediction model is configured to refine over time using continuous learning based on the user's physiological and environmental data history. In an embodiment, an environmental context analysis unit is configured to integrate data from vehicle onboard systems to determine a user's driving status and adjust the sensitivity of the personalized alerts accordingly. In an embodiment, the personalized alert is further configured to reduce false positives in low-risk environments by lowering the alert threshold during low-activity conditions such as stationary work.

Figure 4:
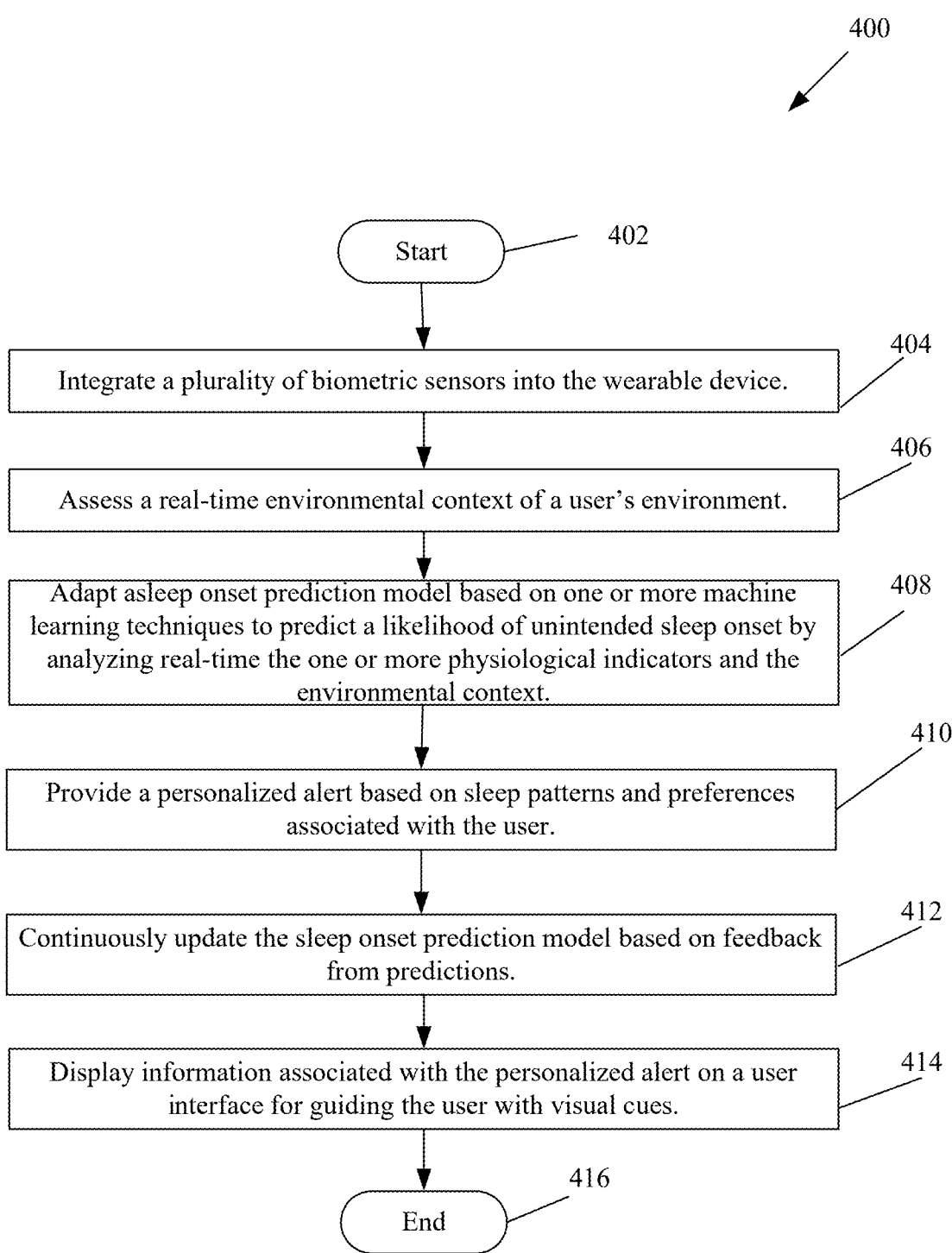
FIG. 4 is a flowchart that illustrates a method for detecting unintended onset of sleep (USL) and providing warnings to a user across multiple environments, in accordance with an embodiment of present disclosure.

FIG. 4 is a flowchart that illustrates a method for detecting unintended onset of sleep (USL) and providing warnings to a user across multiple environments, in accordance with an embodiment of present disclosure. The method begins at the start of step 402 and proceeds to step 304. At step 404, integrate a plurality of biometric sensors into the wearable device. At step 406, an electronic device assesses the real-time environmental context of a user's environment. At step 408, an electronic device adapts asleep onset prediction model based on one or more machine learning techniques to predict a likelihood of unintended sleep onset by analyzing real-time the one or more physiological indicators and the environmental context. At step 410, an electronic device provides a personalized alert based on sleep patterns and preferences associated with the user. At step 412 electronic device continuously updates the sleep onset prediction model based on feedback from predictions. Electronic device displays information associated with the personalized alert on a user interface for guiding the user with visual cues. Control passes end step 414.

A working example of the present disclosure is demonstrated using a smartwatch equipped with a system for detecting unintended sleep onset (USL). Consider a user, such as a traveling salesman, who alternates between long-distance driving and extended desk work for client communications. The smartwatch integrates multiple biometric sensors, including a heart rate monitor, an eye movement tracker, and a micro-vibration detector. The present disclosure also utilizes external sensors such as GPS, accelerometers, and ambient light detectors to assess environmental context. In Driving Scenario: while driving, the system continuously monitors the user's physiological indicators, such as heart rate variability (HRV), blink duration, and micro-vibrations. For instance, the HRV drops progressively from 50 ms to 40 ms, while blink duration averages 300 ms, exceeding the user's normal range of 200 ms. The GPS confirms a highway-speed travel of 70 mph, while the accelerometer detects consistent forward motion, identifying the environment as "high-risk." Using machine learning, the system predicts an 85% likelihood of unintended sleep onset. The present disclosure dynamically increases alert sensitivity, initiating a personalized warning with a moderate vibration and an 80-decibel auditory tone. If the user does not respond, the alert escalates with stronger vibrations, a louder auditory cue, and a visual notification urging the user to pull over. Simultaneously, the system logs the event to refine future predictions. If enabled, a notification is sent to a third party, such as a supervisor or family member, including the user's location and status.

In Desk Scenario: In the desk environment, the system identifies the user's low-risk setting using ambient light levels and the absence of movement from the accelerometer. During prolonged inactivity, such as sustained HRV below 45 ms and increasing blink duration, the system predicts drowsiness at the workstation. Instead of escalating alerts as in the driving scenario, the system adapts by delivering milder notifications, such as a gentle vibration and a soft auditory tone, to avoid disturbing others in the workspace. To re-engage the user, the system may activate a cognitive stimulus, such as a non-distracting puzzle or auditory challenge. If drowsiness persists, the system logs the incident and adjusts its sensitivity thresholds to align with the user's work environment. Adaptability Across Use Cases: The system is designed to operate seamlessly in various environments, including hospitals, classrooms, or other settings where detecting drowsiness can enhance safety or productivity. For example: In hospitals, the present disclosure can notify medical staff of fatigue during critical operations. In classrooms, it can assist instructors in identifying students who may be struggling with focus. The same adaptability allows the system to reduce false positives in low-risk environments, such as during stationary tasks, by lowering alert thresholds appropriately. Continuous learning ensures that the device refines its prediction model over time, tailoring alerts to the user's habits, preferences, and environmental contexts.

Another example of the present disclosure, imagine a scenario where a wearable smartwatch equipped with biometric and environmental sensors is worn by a user driving on a highway. The device monitors key physiological indicators such as heart rate variability (HRV), eye movement, and micro-vibrations, alongside environmental factors like speed and motion detected by GPS and accelerometers. If the system detects prolonged slow eye blinks, decreased HRV, and steady motion indicating highway driving, the system identifies this as a high-risk context. The alert sensitivity dynamically increases. The smartwatch triggers a vibration alert paired with an auditory cue, prompting the user to take immediate corrective action. If the user does not respond (e.g., HRV continues to drop, or eye blinks become longer) the system escalates the alert by intensifying vibrations and increasing auditory volume. Simultaneously, a visual notification advises the user to pull over.

In contrast, if the same user is at a desk and similar drowsiness patterns are detected, the system categorizes this as a low-risk context. Instead of intense alerts, the device provides a subtle vibration or visual notification and suggests taking a short walk or playing a quick mental game like a memory challenge to regain alertness. If the user's preferences allow, the device might even propose a controlled nap of 15-20 minutes and track when to wake them for optimal alertness. This adaptability ensures appropriate alert mechanisms tailored to the activity's risk level, enhancing user safety in high-stakes environments (e.g., driving) while optimizing performance and comfort in low-stakes settings (e.g., desk work).

Various embodiments of the disclosure encompass numerous advantages including detecting unintended sleep onset (USL) and providing timely warnings. One of the primary advantages is its integration of multiple biometric sensors such as heart rate variability, eye movement, and micro-vibrations along with environmental sensors, including GPS, accelerometers, and ambient light sensors. This allows the system to continuously monitor both physiological and environmental factors in real-time, leading to more accurate detection of drowsiness compared to conventional methods that rely on a limited set of indicators.

Another significant advantage is the machine learning-based prediction model, which dynamically adjusts its sensitivity based on the user's environment. This context-aware system ensures that drowsiness detection is more sensitive in high-risk environments, such as during driving, while being less sensitive in low-risk situations like desk work, thereby reducing false positives and improving overall reliability. Additionally, the present disclosure provides personalized warnings tailored to individual user preferences, including vibration, auditory, or visual alerts, ensuring that notifications are effective and aligned with the user's specific sleep patterns and behavior.

The present disclosure focuses on practical applications involving the integration of advanced biometric sensors and environmental data to address the real-world problem of detecting unintended sleep onset and providing personalized warnings. The present disclosure goes beyond theoretical concepts by offering a functional system that monitors multiple physiological indicators, such as heart rate variability, eye movement, and micro-vibrations, along with environmental factors like GPS data, accelerometers, and ambient light. This combination of sensors allows for a comprehensive analysis of both the user's physical state and surroundings, providing a solution that goes beyond what a skilled professional could achieve by merely combining known methods.

Furthermore, the machine learning component, which dynamically adjusts sensitivity based on environmental context and user feedback, represents a sophisticated solution that adapts to different scenarios, such as driving or working in a stationary environment. This level of adaptability and the continuous refinement of the prediction model through user-specific data and past interactions is not something a skilled person would naturally consider or implement without detailed technical insight. The personalized warning mechanism, which tailors' alerts based on the user's unique sleep patterns and environment, adds an additional layer of complexity and user-centric functionality, distinguishing it from conventional solutions that rely on generic thresholds and one-size-fits-all approaches.

The present disclosure's ability to dynamically adjust its drowsiness detection and alert system based on real-time data and environmental context, combined with continuous learning and personalized feedback, introduces a novel approach that a person skilled in the art would not naturally arrive at using existing technologies. The present disclosure requires a detailed understanding of sensor integration, machine learning, and adaptive systems, making it a significant advancement over traditional methods.

A person with ordinary skills in the art will appreciate that the systems, modules, and sub-modules have been illustrated and explained to serve as examples and should not be considered limiting in any manner. It will be further appreciated that the variants of the above disclosed system elements, modules, and other features and functions, or alternatives thereof, may be combined to create other different systems or applications.

Those skilled in the art will appreciate that any of the aforementioned steps and/or system modules may be suitably replaced, reordered, or removed, and additional steps and/or system modules may be inserted, depending on the needs of a particular application. In addition, the systems of the aforementioned embodiments may be implemented using a wide variety of suitable processes and system modules, and are not limited to any particular computer hardware, software, middleware, firmware, microcode, and the like. The claims can encompass embodiments for hardware and software, or a combination thereof.

While the present disclosure has been described with reference to certain embodiments, it will be understood by those skilled in the art that various changes may be made, and equivalents may be substituted without departing from the scope of the present disclosure. In addition, many modifications may be made to adapt a particular situation or material to the teachings of the present disclosure without departing from its scope. Therefore, it is intended that the present disclosure is not limited to the particular embodiment disclosed, but that the present disclosure will include all embodiments falling within the scope of the appended claims.

What is claimed is:

1. A method for detecting unintended onset of sleep (USL) and providing warnings to a user across multiple environments, the method comprising:

integrating, by a processor of a wearable device, a plurality of biometric sensors into the wearable device, wherein the plurality of biometric sensors is configured to continuously monitor one or more physiological indicators of drowsiness associated with a user, wherein the one or more physiological indicators comprises a heart rate variability, an eye movement, and a micro-vibrations;

assessing, by the processor, a real-time environmental context of a user's environment by integrating data from one or more external sensors to distinguish between different environmental contexts, wherein the real-time environmental context comprises a moving vehicle, a stationary workspace, and a classroom, wherein the one or more external sensors comprises GPS, accelerometers, and ambient light sensors;

adapting, by the processor, a sleep onset prediction model based on one or more machine learning techniques to predict a likelihood of unintended sleep onset by analyzing real-time the one or more physiological indicators and the environmental context, wherein the sleep onset prediction model is configured to dynamically adjust a sensitivity based on the real-time environmental context; and providing, by the processor, a personalized alert based on sleep patterns and preferences associated with the user, wherein the personalized alert comprises a vibration, an auditory cue, and a visual notification which is tailored to the user's environment and a historical sleep behavior;

continuously updating, by the processor, the sleep onset prediction model based on feedback from the user and outcomes of prior personalized alerts to improve the accuracy of future predictions; and displaying, by the processor, information associated with the personalized alert on a user interface for guiding the user with visual cues.

2. The method for detecting unintended onset of sleep (USL) and providing warnings to a user across multiple environments, as claimed in claim 1, wherein the wearable device is a smartwatch, smart glasses, or a smart ring.

3. The method for detecting unintended onset of sleep (USL) and providing warnings to a user across multiple environments, as claimed in claim 1, wherein the sleep onset prediction model increases alertness thresholds while detecting that the user is in a high-risk environment.

4. The method for detecting unintended onset of sleep (USL) and providing warnings to a user across multiple environments, as claimed in claim 1, wherein an environmental context analysis unit distinguishes between high-activity and low-activity environments by monitoring environmental triggers.

5. The method for detecting unintended onset of sleep (USL) and providing warnings to a user across multiple environments, as claimed in claim 1, wherein the personalized alert is configured to provide customizable alerts based on the user's preferences, including adjusting the intensity of vibration or auditory cues.

6. The method for detecting unintended onset of sleep (USL) and providing warnings to a user across multiple environments, as claimed in claim 1, wherein the wearable device is further configured to notify a third party comprising a supervisor or instructor, when the unintended sleep onset is detected in non-driving environments.

7. The method for detecting unintended onset of sleep (USL) and providing warnings to a user across multiple environments, as claimed in claim 1, further comprising a cognitive stimulus unit configured to provide non-distracting mental challenges or auditory cues designed to re-engage the user's focus when detected as stationary and drowsy.

8. The method for detecting unintended onset of sleep (USL) and providing warnings to a user across multiple environments, as claimed in claim 1, wherein the sleep onset prediction model is configured to refine over time using continuous learning based on the user's physiological and environmental data history.

9. The method for detecting unintended onset of sleep (USL) and providing warnings to a user across multiple environments, as claimed in claim 1, wherein an environmental context analysis unit is configured to integrate data from vehicle onboard systems to determine a user's driving status and adjust the sensitivity of the personalized alerts accordingly.

10. The method for detecting unintended onset of sleep (USL) and provid-ing warnings to a user across multiple environments, as claimed in claim 1, wherein the personalized alert is further configured to reduce false positives in low-risk environments by lowering the alert threshold during low-activity conditions.

\* \* \* \* \*